(12) United States Patent
Gao

(10) Patent No.: US 7,810,817 B1
(45) Date of Patent: Oct. 12, 2010

(54) HOLDER FOR REPLACEABLE TOOLS

(75) Inventor: Hua Gao, Fox Point, WI (US)

(73) Assignee: Bradshaw Medical, Inc., Kenosha, WI (US)

(*) Notice: Subject to any disclaimer, the term of this patent is extended or adjusted under 35 U.S.C. 154(b) by 996 days.

(21) Appl. No.: 11/601,932

(22) Filed: Nov. 20, 2006

(51) Int. Cl.
B23B 31/22 (2006.01)
(52) U.S. Cl. ........................................ 279/75; 279/905
(58) Field of Classification Search ................. 279/22, 279/30, 69–75, 81, 82, 905; B23B 31/22, B23B 31/107
See application file for complete search history.

(56) References Cited

U.S. PATENT DOCUMENTS

| 685,677 | A | * | 10/1901 | Furbish | 279/69 |
| 922,936 | A | * | 5/1909 | Miller | 279/82 |
| RE13,724 | E | * | 5/1914 | Lindberg | 279/75 |
| 1,345,583 | A | * | 7/1920 | Church | 279/74 |
| 1,539,439 | A | * | 5/1925 | Smith | 279/74 |
| 1,635,909 | A | * | 7/1927 | Tobeler | 279/30 |
| 1,781,442 | A | * | 11/1930 | Currier | 279/75 |
| 2,751,229 | A | * | 6/1956 | Schultz | 279/75 |
| 2,807,473 | A | * | 9/1957 | Kiehne | 279/82 |
| 3,583,715 | A | * | 6/1971 | Jahrl | 279/75 |
| 3,658,351 | A | * | 4/1972 | Benjamin et al. | 279/75 |
| 3,767,218 | A | | 10/1973 | Linthicum | |
| 3,947,047 | A | * | 3/1976 | Hultman | 279/75 |
| 4,287,923 | A | * | 9/1981 | Hornung | 81/429 |
| 4,930,261 | A | * | 6/1990 | Tiegs et al. | 451/256 |
| 5,893,851 | A | * | 4/1999 | Umber et al. | 606/80 |
| 5,947,484 | A | | 9/1999 | Huggins | |
| 5,975,815 | A | * | 11/1999 | Zierpka et al. | 408/226 |
| 5,996,452 | A | | 12/1999 | Chiang | |
| 6,179,302 | B1 | * | 1/2001 | Gauthier et al. | 279/75 |
| 6,193,242 | B1 | * | 2/2001 | Robison | 279/137 |
| 6,224,303 | B1 | | 5/2001 | Wheeler | |
| 6,234,491 | B1 | * | 5/2001 | Wheeler | 279/143 |
| 6,241,434 | B1 | * | 6/2001 | Ajimi | 408/238 |
| 6,302,408 | B1 | * | 10/2001 | Zierpka | 279/75 |
| 6,311,989 | B1 | | 11/2001 | Rosanwo | |
| 6,457,916 | B2 | | 10/2002 | Wienhold | |
| 6,612,586 | B2 | * | 9/2003 | Liou | 279/22 |
| 6,695,321 | B2 | * | 2/2004 | Bedi et al. | 279/22 |
| 6,722,667 | B2 | | 4/2004 | Cantlon | |
| 6,953,196 | B1 | | 10/2005 | Huang | |
| 6,966,562 | B1 | * | 11/2005 | Wienhold | 279/75 |
| 7,086,313 | B2 | * | 8/2006 | Cantlon | 81/438 |
| 7,469,909 | B2 | * | 12/2008 | Strauch et al. | 279/75 |

(Continued)

FOREIGN PATENT DOCUMENTS

WO   WO 9924200 A1 * 5/1999

Primary Examiner—Eric A Gates
(74) Attorney, Agent, or Firm—Arthur J. Hansmann

(57) ABSTRACT

A holder for replaceable tools and having a body with an opening along a longitudinal axis for snugly and individually receiving various tools. Two balls are on the body for engagement with the tools, and there is a projection into the opening for contacting the tool in a location diametrically opposite the location of the balls. A sleeve member is slideable on the body, and has two sets of camming ramps and cylindrical surfaces extending radially over the balls for controlling the radially location of the balls relative to the tool. The tool has a surface for abutting the body projection to thereby hold the tool free of radial deviation relative to the holder axis.

18 Claims, 3 Drawing Sheets

U.S. PATENT DOCUMENTS

| | | | |
|---|---|---|---|
| 7,669,860 B2 * | 3/2010 | Chiang | 279/143 |
| 2002/0067008 A1 | 6/2002 | Frenzel | |
| 2004/0013485 A1 * | 1/2004 | Zierpka | 408/240 |
| 2004/0164503 A1 | 8/2004 | Chiang | |
| 2004/0262856 A1 | 12/2004 | Cantion | |

* cited by examiner

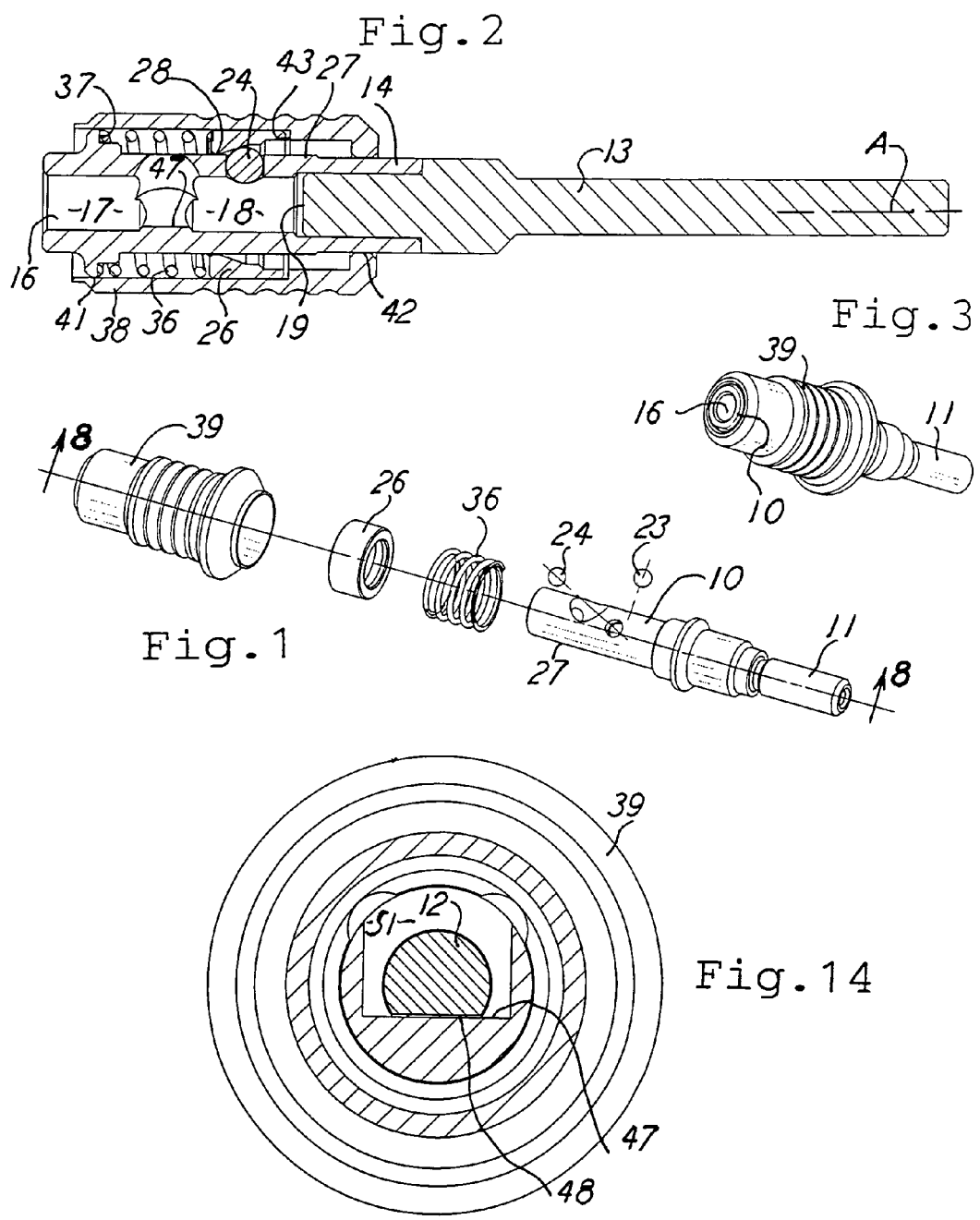

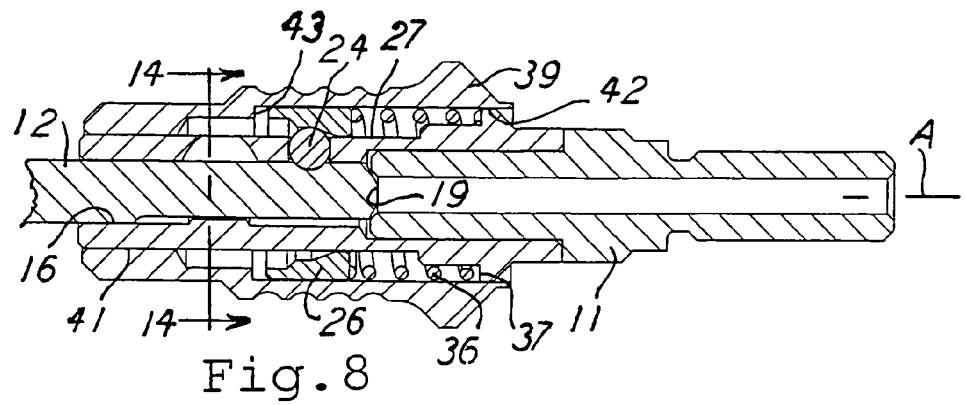
Fig. 8
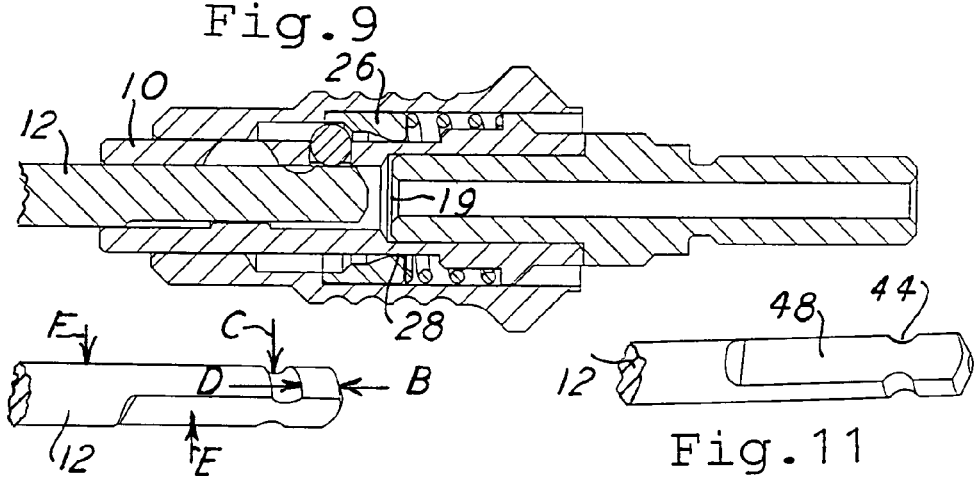
Fig. 9
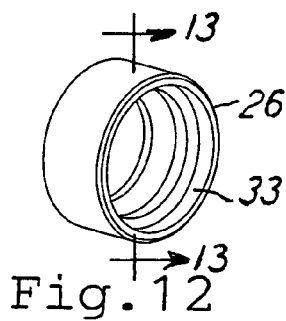
Fig. 10
Fig. 11
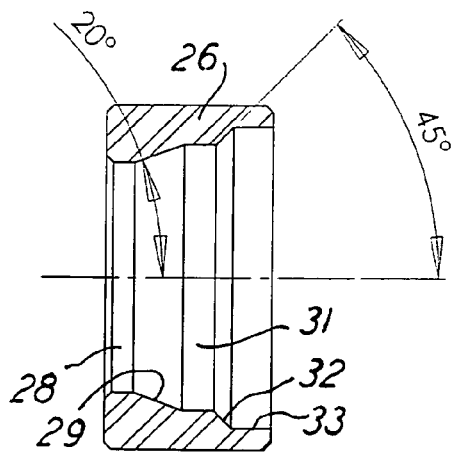
Fig. 12
Fig. 13

HOLDER FOR REPLACEABLE TOOLS

This invention relates to holders for replaceable tools, such as tool chucks. The holder may be an adapter which is releasably connected to and driven by a conventional driver, such as a hand-rotated handle.

BACKGROUND OF THE INVENTION

The prior art is already aware of tool holders, including adapters, which are intended for radially and axially stabilizing replaceable and rotatable tools. Further, there are holders which utilize a spring-urged ball or balls for the tool stabilizing effect. In those occurrences, the balls exert the radial forces against the tool, and the holder tool-receiving curvature defining the holder bore provides the reaction for radially forcing onto the tool. Thereby, the holding effort on the tool is limited to the holding action of the balls and the curvature of the holder body bore, and thus the holding action is limited in its precision.

The present invention improves upon the prior art in that it is precise in holding the various tools which are inserted into the holder. Those tools themselves may be imprecise in their configuration and therefore difficult to hold in radial and axial accuracy and consistency, and this invention avoids those problems. Both radial and axial play are avoided.

Further, this invention can be reduced to an actual construction which produces a precise, efficient, and both a radial and axial holding construction. This invention overcomes the tendency for the tool to be inadvertently pulled out of the holder even though the holder is set in its holding mode.

Still further, this invention provides for the manufacture of the holder in a precise and feasible manner for including the herein-mentioned features which render precise holding, as mentioned. Also, the holder is actuated in a manner at least similar to that of the popular prior art holders which have a sliding sleeve-type control member on the holder for producing the holding and release of the inserted tools. So no new and different familiarizing by the user is required. In this regard, the sliding control member includes both the tool holding and the tool release features. Further, the holder can be arranged with its sliding control member which slides in an axial direction for enhancing the axial holding force on the tool and thereby avoid inadvertent forceful release of the tool from the holder.

Also, this holder can be made in an efficient manner to produce its uniqueness without elaborate manufacturing procedures. The precision herein achieved is important for holders used in the medical arts.

BRIEF DESCRIPTION OF THE DRAWINGS

FIG. 1 is an exploded perspective view of an embodiment of this invention.

FIG. 2 is a longitudinal sectional view of another embodiment of this invention.

FIG. 3 is a perspective view of the assembly of that shown in FIG. 1.

FIG. 8 is a longitudinal sectional view taken on a plane designated by the line 8-8 of FIG. 1 when assembled, and with the tool added thereto.

FIG. 9 is a longitudinal sectional view like FIG. 8 but with parts in positions slightly different from FIG. 8.

FIGS. 10 and 11 are perspective views of the tool which can be held by the holders of FIGS. 1 and 2.

FIG. 12 is an enlarged perspective view of a part shown in FIG. 1.

FIG. 13 is an enlarged section view taken along a plane designated by the line 13-13 of FIG. 12.

FIG. 14 is an enlarged section view taken along a plane designated by the line 14-14 of FIG. 8.

DETAILED DESCRIPTION OF THE PREFERRED EMBODIMENTS

Figure 4:
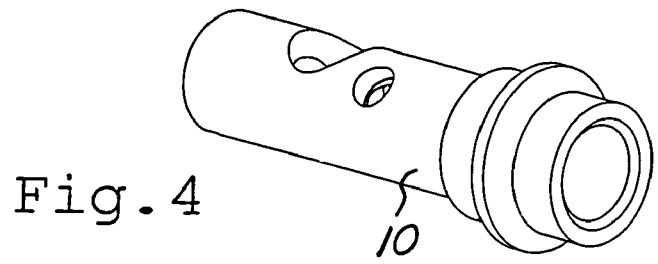
FIGS. 4, and 5 are enlarged perspective views of a part shown in FIG. 1.

The invention is shown in two embodiments, as seen in FIGS. 1 and 2. In FIG. 1, there is a cylindrical and elongated body 10 having a central axis A. A conventional driving member 11 can be suitable arranged and connected to the body 10 and, in turn, a conventional but unshown driver can be connected to the member 11 for rotating the body in the operation of the entire shown holder. Likewise, FIG. 2 shows a driving member 13. Somewhat like the FIG. 8 embodiment, the FIG. 2 embodiment has an elongated and cylindrically shaped body 14 which receives the tool 12 and all is rotated by the member 13 and about the longitudinal axis A. For both embodiments, FIGS. 8-11 show the work tool 12 which is insertable into the bodies 10 and 14 at the respective body opening ends 16, though the tool is not shown in FIG. 2 but it will be understood to be there. The effect is to rotationally drive the tool 12 and to hold it axially and radially in both embodiments.

Both bodies 10 and 14 both have two longitudinal interior openings 17 and 18 in axial alignment with each other and both openings snugly slideably receive the tool 12. The members 11 and 13 present an abutment 19 at the end of the opening 18. The inserted tool 12 will contact the abutment 19 and thereby limit the Insertable axial movement of the tool in each embodiment, and rightward as seen in FIGS. 2 and 9.

Figure 5:
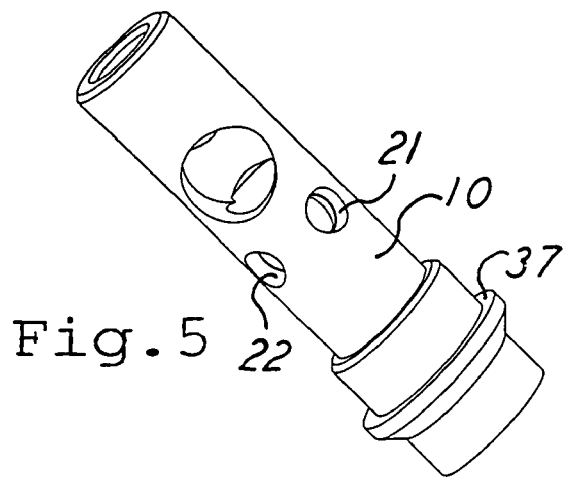
Figure 6:
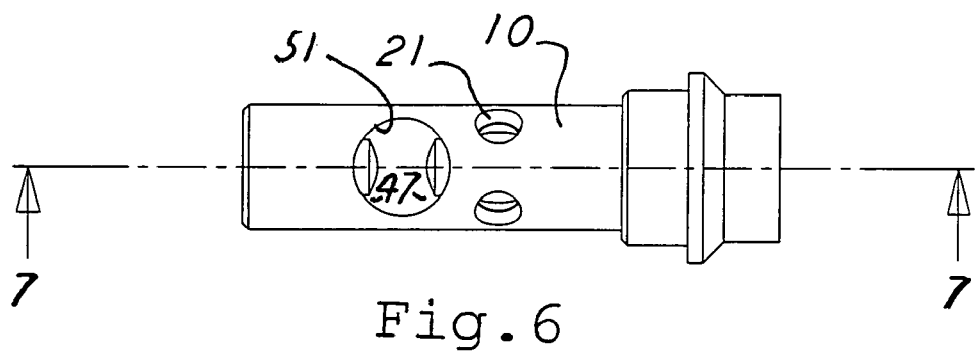
FIG. 6 is a side elevation view of the part shown in FIGS. 4 and 5.
Figure 7:
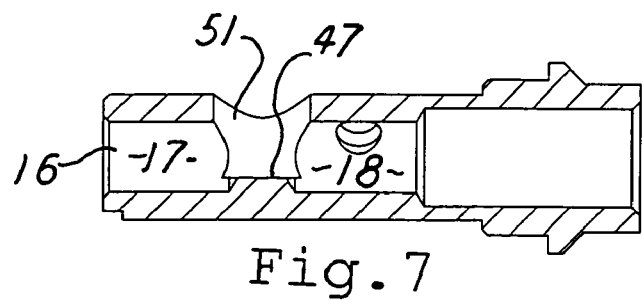
FIG. 7 is a section view taken along a plane designated by the line 7-7 of FIG. 6.

FIGS. 5 and 6 best show that both bodies 10 and 14 each have two holes 21 and 22 extending therethrough and to the opening 18. Two detents, in the form of two balls 23 and 24, are respectively disposed in and are radially movable in the holes 21 and 22, in the usual manner. Also, in the usual manner, the holes 21 and 22 are restricted adjacent the opening 18 to keep the balls from fully passing into the opening 18, and the balls move toward the axis A no closer than that shown in FIG. 2.

Each body 10 and 14 has a cylindrical member 26 axially slideably thereon, though the member 26 faces in axially opposite directions between the two embodiments. As shown, the bodies respectively have cylindrical outer surfaces 27, and the member 26 has an inner cylindrical surface 28 which is snugly slideable on the respective body surfaces 27. The member 26 extends over the balls 23 and 24 for restraining the balls against radial outward movement.

For ball restraining, FIG. 13 best shows that the member 26 has a first camming ramp 29 and it also has a cylindrical surface 31 contiguous to the ramp 29. In the FIG. 2 arrangement of the member 26, the ramp faces toward the abutment 19. The member also has a second camming ramp 32, and it has a cylindrical surface 33. The ramps 29 and 32 are angulated relative to the axis A but face inward toward the axis A, as shown. The foregoing can all be sequentially contiguous, and the diametrical dimensions of the two ramps and all cylindrical surfaces are such that they can contact the balls between the axial alternate positions of FIGS. 2, 8, and 9 and thereby hold the balls against the tool such as is apparent between FIGS. 8 and 9. The angulation of the ramp or incline 29 can be approximately 20 degrees, and that of the ramp 32 can be 45 degrees with the main holding force exerted by the ramp 29 at that radially optimum angle.

A spring 36 is disposed and anchored between a shoulder 37, on the bodies 10 and 14, and against the member 26. So the spring exerts a force on the member 26 to cause the ramp 29 to engage the balls and thereby releasably hold the work tool 12 in the holder. In the FIG. 2 embodiment, under the force of the spring 36, because the ramp 29 faces the abutment 19 the balls even moreso force on the tool toward the abutment 19 for secure axial holding of the tool 12.

Cylindrical control sleeves 38 and 39 extend over the members 26, and the springs 36 and are in sliding contact with the bodies at the circular surfaces at 41 and 42. Axial sliding movement of the sleeves 38 and 39 causes circular shoulders 43 to abut the member 26 to thereby compress the spring 36 and axially move the member 26 to thereby eventually release the balls from their locking positions with the tool 12. For that releasing, in FIG. 2, the sleeve 38 is slid leftward by a likely pushing action from the operator, and, in FIG. 8, the sleeve 39 is slid rightward by a likely pulling action from the operator.

When the members 26 are initially axially moved off the holding positions of FIGS. 2 and 8, the ramp 29 radially releases the balls 23 and 24 but does not fully release the tool 12 because the balls will still be held in the groove 44 in the tool by the ramp 29. Likewise, the balls are still held in the groove 44 when the member 26 is slid to have its cylindrical surface 31 over the balls. Such is the dimensioning of the diameter of the balls, the radial position of the surface 31 from axis A, and the location of the tool groove so that the tool is axially restrained. In FIG. 8, without holding the balls by the cylindrical surface 31, the tool can be axially strongly pulled out of the body by virtue of the axial force on the tool being applied to the ball at the ramp 29 which can axially displace the member 26 in response to a pulling force on the tool because of the inclined orientation of the ramp 29. With further axial movement of the member 26 toward the FIG. 9 position, the balls will engage the second ramp 32 and be radially released, as well as having the balls adjacent the second cylindrical surface 33, as in the FIG. 9 position. At that mode, the tool 12 is then fully released, as shown in FIG. 9. Of course, the FIG. 9 showing is also depicting the insertion of the tool into the body 10, and for that the sleeve 39 was pulled rightwardly by the user to thereby retract the member 26 and the balls.

The bodies 10 and 14 have a projection 47 extending between the openings 17 and 18, as seen in the sectional views. The projections are flat, that is, two dimensional planar, and extend both along and across the body openings, as seen in FIGS. 2, 7, 8 and 14. The tool 12 also can have a flat 48 disposed in full planar contact with the body projection 47. Those flats on the bodies and the tool are diametrically and axially offset from the balls 23 and 24 which therefor force the tool downward against the projection 47. Still further, the tool is snug in the openings 17 and 18 and therefor has radial holding forces thereagainst. FIG. 10 shows the plurality of forces acting on the tool 12 such as the axial force B by the abutment 19, and particularly emphasized by the FIG. 2 embodiment; the axial and radial forces C and D, respectively, by the balls in the tool groove 44; the radial force E by the projection 47; and the radial force F from the upper portions of the circular wall defining the opening 17.

To accurately and efficiently provide the projection 47, a hole 51 is formed in the bodies down to the formation of the projection 47. So openings 17 and 18 can be formed from respective ends of the respective bodies 10 and 14 up to the projection 47.

In conformance with requirements, two embodiments are shown herein. However, it will be apparent that changes can be made in the various parts and procedures, so the inventive scope should be in accord with the following claims and the equivalents thereof.

What is claimed is:

1. In a holder for replaceable tools, the improvement comprising: a body having an elongated axis with an opening extending along said axis for snugly receiving a work tool inserted axially into said opening and with said body having a hole extending through said body to said opening, a circular member on said body and being axially movable relative to said body along said axis and having a camming ramp facing said opening and being disposed radially outward with respect to said hole, a ball disposed in said hole and being in respective contact with said camming ramp and exposed to said opening and being positionable into contact with the work tool for effecting a first radially directed axially inward force on the work tool and for effecting an axial holding force on the work tool, a spring for urging said member axially and thereby urge said ball into its contact with the work tool for holding the work tool in said body, the work tool having an arcuate recess for receiving said ball for effecting the axial holding force on the work tool, said circular member having a cylindrical surface adjacent to said camming ramp and facing toward said axis and extending coaxially relative to said axis and being circularly disposed for confining said ball in said arcuate recess upon axial movement of said circular member to a position where said ball is free of being disposed in contact with said camming ramp and thereby further axially have said ball hold the work tool, and said circular member having an additional camming ramp and an additional cylindrical surface in line with each other and disposed axially adjacent the first-mentioned said cylindrical surface and being radially spaced further out than that of said first-mentioned camming ramp and said first-mentioned cylindrical surface for freeing said ball relative to the work tool upon axial movement of said member and thereby free the work tool relative to said body, said body having a protrusion radially extending into said opening at a location axially spaced from the axial location of said detent and facing said axis for forcing onto the work tool in a second radially directed axially inward force in a direction counter to that of the radial direction of said first force and thereby have two radially directed forces at two respective axially spaced-apart locations on the work tool, and said body having a second hole extending into said opening at a location diametrically opposite the location of said protrusion for access to said protrusion by a forming tool for forming said protrusion.

2. The holder for replaceable tools as claimed in claim 1, further comprising: said protrusion being a flat surface extending into said opening and extending parallel to said axis.

3. The holder for replaceable tools as claimed in claim 2, further comprising:

the work tool having a flat surface thereon for contacting said protrusion upon insertion into said opening.

4. The holder for replaceable tools as claimed in claim 1, further comprising: there being two said balls limitedly movably radially confined in said body and being located on said body in respective locations adjacent each other and only substantially diametrically opposite the location of said protrusion.

5. The holder for replaceable tools as claimed in claim 1, further comprising: said body having a recess for receiving said ball and thereby axially restricting said ball.

6. In a holder for replaceable tools, the improvement comprising:
   a body having an elongated axis with an opening extending along said axis for snugly receiving a work tool inserted axially into said opening and with said body having a first hole extending through said body to said opening,
   a circular member on said body and being axially movable relative to said body along said axis and having a camming ramp facing said opening and being disposed radially outward with respect to said first hole,
   a detent disposed in said first hole and being in respective contact with said camming ramp and exposed to said opening and being positionable into contact with the work tool for effecting a first radially directed axially inward force on the work tool and for effecting an axial holding force on the work tool,
   a spring for urging said member axially and thereby urge said detent into its contact with the work tool for holding the work tool free of radial and axial movement relative to said axis,
   said body having a protrusion radially extending into said opening at a location axially spaced from the axial location of said detent and facing said axis for forcing onto the work tool in a second radially directed axially inward force in a direction counter to that of the radial direction of said first force and thereby have two radially directed forces at two respective axially spaced-apart locations on the work tool, and
   said body having a second hole extending into said opening at a location diametrically opposite the location of said protrusion for access to said protrusion by a forming tool for forming said protrusion.

7. The holder for replaceable tools as claimed in claim 6, further comprising: said detent being two balls limitedly movably radially confined in said body and being located on said body in respective locations adjacent each other and substantially diametrically opposite the location of said protrusion.

8. The holder for replaceable tools as claimed in claim 6, further comprising: said member having a cylindrical surface contiguous to said camming ramp and being disposed to extend radially of and in contact with said detent and for thereby restricting said detent from moving both radially outward and axially relative to said axis.

9. The holder for replaceable tools as claimed in claim 8, further comprising:
   said member having an additional camming ramp and an additional cylindrical surface contiguous thereto for restricting said detent from moving both radially outward and axially relative to said axis.

10. The holder for replaceable tools as claimed in claim 6, further comprising: said member having an additional camming ramp facing said opening and being disposed radially outward with respect to said hole for restricting said detent from moving radially outward relative to said axis.

11. The holder for replaceable tools as claimed in claim 6, further comprising: said detent being a ball and said work tool having an arcuate recess for receiving said ball for effecting the axial holding force on said work tool, and said circular member having a cylindrical surface adjacent to said camming ramp and facing toward said axis and extending coaxially relative to said axis and being circularly disposed for confining said ball in said arcuate recess upon axial movement of said circular member to a position where said ball is free of being disposed in contact with said camming ramp and thereby further axially have said ball hold said work tool.

12. The holder for replaceable tools as claimed in claim 11, further comprising, said circular member having an additional camming ramp and cylindrical surface axially adjacent the first-mentioned camming ramp and cylindrical surface and being radially spaced further out than that of said first-mentioned camming ramp and said cylindrical surface for freeing said ball relative to said work tool upon axial movement of said member and thereby free said work tool relative to said body.

13. The holder for replaceable tools as claimed in claim 12, further comprising:
   said camming ramps being disposed at respective angulations relative to said axis and with said additional camming ramp being at an angle which is less than that of the other said camming ramp.

14. The holder for replaceable tools as claimed in claim 6, further comprising:
   said protrusion being a flat surface extending into said opening and extending parallel to said axis.

15. The holder for replaceable tools as claimed in claim 14, further comprising:
   the work tool having a flat surface thereon for extending in contact with and along said protrusion upon insertion into said opening.

16. The holder for replaceable tools as claimed in claim 15, further comprising:
   said detent being two balls limitedly movably radially confined in said body and being located on said body in respective locations adjacent each other and only substantially diametrically opposite the location of said protrusion and axially spaced from said second hole.

17. The holder for replaceable tools as claimed in claim 6, said circular member having a cylindrical surface adjacent to said camming ramp and facing toward said axis and extending axially relative to said axis and being circularly disposed for confining said ball in an arcuate recess upon axial movement of said circular member to a position where said ball is free of being disposed in contact with said camming ramp and thereby have said ball further axially hold the work tool.

18. The holder for replaceable tools as claimed in claim 17, further comprising: said circular member having an additional camming ramp and an additional cylindrical surface in line with each other and disposed axially adjacent the first-mentioned said cylindrical surface and being radially spaced further out than that of said first-mentioned camming ramp and said cylindrical surface for freeing said ball relative to the work to tool upon axial movement of said member and thereby free the work piece relative to said body.

* * * * *